(12) United States Patent
Kim et al.

(10) Patent No.: US 10,286,021 B2
(45) Date of Patent: May 14, 2019

(54) **COMPOSITION FOR PREVENTION OR TREATMENT OF ARTHRITIS, CONTAINING *SARGASSUM SERRATIFOLIUM* EXTRACT AS ACTIVE INGREDIENT**

(71) Applicant: PUKYONG NATIONAL UNIVERSITY INDUSTRY—UNIVERSITY COOPERATION FOUNDATION, Busan (KR)

(72) Inventors: Hyeung-Rak Kim, Busan (KR); Mi-Sung Kwon, Busan (KR); Eun-Ji Joung, Busan (KR)

(73) Assignee: Pukyong National University Industry-University Cooperation Foundation (KR)

( * ) Notice: Subject to any disclaimer, the term of this patent is extended or adjusted under 35 U.S.C. 154(b) by 0 days.

(21) Appl. No.: 15/578,200

(22) PCT Filed: Feb. 11, 2016

(86) PCT No.: PCT/KR2016/001371
§ 371 (c)(1),
(2) Date: Nov. 29, 2017

(87) PCT Pub. No.: WO2017/073849
PCT Pub. Date: May 4, 2017

(65) Prior Publication Data
US 2018/0221424 A1    Aug. 9, 2018

(30) Foreign Application Priority Data

Oct. 30, 2015 (KR) .................. 10-2015-0152164

(51) Int. Cl.
*A61K 36/03* (2006.01)
*A61P 19/02* (2006.01)

(52) U.S. Cl.
CPC .............. *A61K 36/03* (2013.01); *A61P 19/02* (2018.01); *A61K 2236/00* (2013.01)

(58) Field of Classification Search
None
See application file for complete search history.

(56) References Cited

U.S. PATENT DOCUMENTS

2010/0247564 A1* 9/2010 Lee .................. A61K 36/03
424/195.17
2014/0336234 A1* 11/2014 Yoshioka ............ A23L 33/10
514/414

FOREIGN PATENT DOCUMENTS

| KR | 1020100131809 A | 12/2010 |
|---|---|---|
| KR | 101057007 B1 | 8/2011 |
| KR | 1020110118064 A | 10/2011 |
| WO | WO2017073849 A1 | 4/2017 |

OTHER PUBLICATIONS

Oh et al. 2016 (Anti-Inflammatory Effect of Ethanolic Extract of Sargassum serratifolium in Lipopolysaccharide-Stimulated BV2 Microglial cells; Journal of Medicinal Food 19(11): 1023-1031). (Year: 2016).*

Joung, Eun-Ji et al. "Anti-inflammatory Effect of Sargachromenol Isolated from Saragassium serratifolium on Lipopolysaccharide-induced Nitric Oxide and Prostaglandin $E_2$ in Raw 2641 Macrophages." DBpia, 5 (2015): 239.

Kusumi, Takenori et al. "Structures of New Plastoquinones from the Brown Alga *Saragassium serratifolium*." Chemisty Letters, (1979): 277-278.

* cited by examiner

*Primary Examiner* — Mary Maille Lyons
(74) *Attorney, Agent, or Firm* — JHK Law; Joseph Hyosuk Kim (57) ABSTRACT

The present invention relates to a composition for the prevention or treatment of arthritis, the composition containing a *Sargassum serratifolium* extract as an active ingredient. The extract of *Sargassum serratifolium* according to the present invention has an excellent activity to reduce or inhibit the activity of IL-1β, IL-6, or TNF-α, which is an inflammatory cytokine, and has an excellent effect alleviating arthritis in an arthritis animal model so that it can be usefully used as a composition for treating arthritis. In addition, there is no cytotoxicity, and toxicity to the drug and side effects are avoided so that it can be safely used even for long-term use, and it is stable in the body.

2 Claims, 10 Drawing Sheets

COMPOSITION FOR PREVENTION OR TREATMENT OF ARTHRITIS, CONTAINING *SARGASSUM SERRATIFOLIUM* EXTRACT AS ACTIVE INGREDIENT

TECHNICAL FIELD

The present invention relates to a composition for preventing or treating arthritis, in which the composition includes an extract of *Sargassum serratifolium* as an active ingredient.

BACKGROUND ART

The human body is made of about 200 joints. The bones meet each other in the joints, which are composed of cartilage, joint capsule, synovial membrane, ligament, tendon, muscle, etc. in order to smoothly move between the bones and play a role in absorbing the impact caused by the movement.

Inflammatory diseases that occur in these joints can be divided largely into chronic rheumatoid arthritis, which is understood to be caused by autoimmunity, infectious arthritis caused by bacterial infection, deformed arthritis caused by degeneration or destruction of articular cartilage or bone due to various causes, and crystalline arthritis caused by deposition of soluble metabolites as crystals in the connective tissue around the joints due to degenerative changes of the connective tissue.

Degenerative arthritis, that is, osteoarthritis, is a disease caused by the destruction of joint tissue due to the increases of synthesis and activity of matrix metalloproteinase (MMP), which degrades the joint matrix in joint cells by the production of inflammatory cytokines, such as, interleukin-1β and tumor necrosis factor-α, while the degeneration of chondrocytes forming joints occurs due to aging, thereby inhibiting the synthesis of type II collagen and proteoglycan, which are matrix materials of joints in chondrocytes.

Further, the arthritis is worsened by the production of nitric oxide because of inflammatory cytokines and by the production of self-amplifying cytokines due to the produced nitric oxide, which leads to the synthesis of more MMPs and promotes the degradation of the joint matrix. At the same time, inflammatory cytokines increase the production of prostaglandin E2 that is a lipid metabolite, and thus, lead to an inflammatory response in arthritis.

Various biochemical phenomena are involved in the inflammatory reaction in vivo. Particularly, the inflammatory reaction is initiated or adjusted by various enzymes, which are related to the inflammatory response produced by immune cells. Specifically, the immune cells migrate to the injured site through the blood vessels with the help of histamine, nitric oxide (NO), prostaglandin E2 (PGE2), etc., and then, begin the inflammatory reaction. The immune cells migrated to the injured site secret cytokines such as tumor necrosis factor-α (TNF-α), interleukin-1β (IL-1β), or interleukin-6 (IL-6) or chemokines such as MIP-1, IL-8, or MCP-1 to destroy direct external invaders or collect other immune cells, thereby initiating the inflammatory response.

In the case where being exposed to inflammatory-inducing substances such as interferon-λ, lipoteichoic acid, and lipopolysaccharide (LPS), which induces the inflammatory reaction, or various inflammation-inducing cytokines, inducible nitric oxide synthase (iNOS) and cyclooxygenase-2(COX-2) are expressed, thereby producing the excess NO and PGE2. The several inflammatory initiators (iNOS, COX-2, TNF-α, IL-6, etc.) promote transcription by activated NF-κB, so that NO is produced more than was needed, thereby causing vasodilation due to shock, tissue damage caused by inflammatory response, mutagenesis, damage of nerve tissue, and the like.

Nitric oxide (NO) is produced from L-arginine and molecular oxygen by NO synthase (NOS). In mammals, there are three types of NOS: neuronal NOS (nNOS), endothelial NOS (eNOS), and inducible NOS (iNOS). nNOS and eNOS are constitutively expressed in nerve cells and endothelial cells. However, iNOS is inductively produced in macrophages or monocytes by exposure to LPS-induced or pro-inflammatory cytokines (Vane et al., 1994). NO produced in iNOS causes inflammation or an immune response, and thus acts as a proliferation inhibitor or a cytotoxic agent of a pathogen that invades the cell. However, it is known that excess NO produced by overexpression of iNOS causes pathological conditions (Kim et al., 2005; Pan et al., 2011). The deleterious effect of excess NO in the cell not only acts as an inflammatory mediator itself, but also reacts with superoxide to produce peroxynitrite. Peroxynitrite may not only cause oxidative damage of intracellular molecules such as proteins, fats and DNA, but also modify normal gene regulation. Thus, overexpression of iNOS as well as large amounts of NO is closely related to pathological conditions associated with various inflammatory diseases (MacMicking et al., 1997; Maeda and Akaike, 1998).

Nuclear factor kappa B (NF-κB) plays a major role in immune and acute inflammatory responses as well as cell growth (Li and Verma, 2002; Makarov, 2001). NF-κB activation promotes the expressions of iNOS and several pro-inflammatory genes (Kim et al., 2005; Makarov, 2001). The activation pathway of NF-κB is such that the inhibitor of κB (IκB)-α kinase is phosphorylated by LPS followed by phosphorylation of IκB-α, and IκB-α phosphorylated by ubiquitin is degraded to cause free NF-κB to move the nucleus, thereby adjust inflammatory related genes (Chen et al., 1995). Activation of another NF-κB occurs via mitogen-activated protein kinases (MAPKs) (Guha and Mackman, 2001) or phosphatidylinositol 3-kinase (PI3K)/protein kinase B (Akt) pathway (Sheu et al., 2005). MAPKs have extracellular signal-regulated kinases (ERKs), c-Jun NH2-terminal kinases (JNKs), and p38 MAPKs, which are involved in transcriptional regulation of inflammatory genes through NF-κB activation (Bhat et al., 1998; Kao et al., 2005; Shin et al., 2010). PI3K is also involved in the production of inflammatory cytokines through NF-κB activation (Cremer et al., 2011; Sheu et al., 2005). PI3K activation phosphorylates the phosphatidylinositide to activate the Akt protein. The activated PI3K/Akt plays a major role in the activation of macrophages (MacMicking et al., 1997; Sheu et al., 2005). Therefore, in order to develop an anti-inflammatory agent, many studies have been carried out to find a substance that inhibits the activation of NK-κB or inhibits activation of MAPKs and Akt which activate NF-κB.

MMPs are proteolytic enzymes that destroy bone and cartilage matrix components and are expressed in cartilage tissues stimulated by inflammatory cytokines in inflammatory disease states, resulting in increased activity. MMPs constitute at least 21 enzymes, being classified into sub-classes including collagenase (MMP-1, 8, and 13), stromelysin (MMP-3, 10, and 11), gelatinase (MMP-2 and 9), and matrix type-1 metalloproteinase (MMP-14). Among them, MMP-2 and MMP-9 are gelatinase subfamily, which is an important enzyme for collagen degradation of cartilage tissue. These two enzymes break down other substrates, such as fibrous collagen I and II, which are abundant in cartilage, and aggrecan.

Rheumatoid and degenerative arthritis are characterized by inflammatory cell infiltration into synovial tissue, which is mediated by chemokines. It is known that chemokines such as monocyte chemoattractant protein-1 (MCP-1) are expressed in the synovial tissue, and they are produced in synovial fibroblasts and the like. Excessive MCP-1, produced by arthritis, causes monocytes and macrophages to come in inflammatory sites and activates these cells to promote the production of inflammatory cytokines, thereby further aggravating the inflammation.

The expression of adhesion molecules such as vascular cellular adhesion molecule 1 (VCAM-1), intercellular adhesion molecule 1 (ICAM-1), and E-selectin in vascular endothelial cells was increased by cytokines in synovial tissues of rheumatoid and degenerative arthritis to induce infiltration of inflammatory cells. Overexpressed ICAM-1 and VCAM-1 are associated with chronic inflammation such as rheumatoid arthritis and degenerative arthritis.

Rheumatoid and degenerative arthritis are chronic systemic inflammatory diseases that cause symmetrical, multiple arthritis, resulting in joint damage and deformation. In the absence of treatment for these arthritis, the progression is poor, indicating a disability of the joint function, and if persistent, disability of the joint function interferes with daily life. In Korea, it is estimated that about 1% of the total population is suffering from rheumatoid arthritis. It is known that the incidence ratio of rheumatoid arthritis is three times higher in women than in men, and it occurs mainly in the 20s and 40s.

The main causes of rheumatoid arthritis have been increasingly revealed, and genetic factors, infections, hormonal abnormalities, etc. are thought to be causative factors. Because of these causative factors, "autoimmune" phenomenon occurs. The autoimmune is a phenomenon that chronic inflammation occurs multiply and lastingly in many parts of the body due to abnormality of immune regulation function of our body.

Meanwhile, drugs used in the treatment of arthritis can be categorized on the basis of the main mechanism of action such as reduction of inflammation, delay of disease progression, and decrease of uric acid concentration. Many neuroarthritis treatment drugs act to reduce inflammation. Inflammation is a pathological process that causes pain, swelling, fever, seizures, and stiffness. Drugs that rapidly relieve inflammation include nonsteroidal anti-inflammatory drugs including aspirin and steroidal anti-inflammatory drugs including cortisone.

Nonsteroidal anti-inflammatory drugs have the effect of relaxing nerve joints and relieving inflammation by reduction of pain. However, because gastrointestinal disorders may occur or abdominal pain may be induced, use thereof is preventive for some people with active peptic ulcer or hemorrhagic lesions in the gastrointestinal portion. Steroidal anti-inflammatory drugs are not used well for degenerative arthritis due to severe side effects such as weight gain and hypertension compared to their effects.

In particular, steroidal anti-inflammatory drugs have nothing to do with the causative treatment of the disease, and may simply induce excessive use of joints by temporarily reducing the pain, which causes destruction of the nerve joints and deterioration of the disorder so that it requires attention in use.

Therefore, conventional therapies used for joint damage such as arthritis have limited effectiveness, involve obvious toxic side effects, cannot be used continuously for a long period of time, and thus their effectiveness is limited. Thus, there is a desperate need for a novel therapeutic method or a therapeutic agent that overcomes the disadvantages of conventional therapeutic methods.

DISCLOSURE

Technical Problem

Accordingly, the inventors of the present invention revealed that *Sargassum serratifolium* suppresses inflammatory cytokines and improves arthritis in arthritic experimental animals, thereby confirming that it can be used as a therapeutic agent for arthritis, and completing the present invention.

Accordingly, an object of the present invention is to provide a pharmaceutical composition for preventing or treating arthritis, in which the pharmaceutical composition includes *Sargassum serratifolium* as an active ingredient.

Another object of the present invention is to provide a health functional food for preventing or ameliorating arthritis, in which the health functional food includes *Sargassum serratifolium* as an active ingredient.

Technical Solution

In order to achieve the above objects, the present invention provides a pharmaceutical composition for preventing or treating arthritis, in which the pharmaceutical composition includes *Sargassum serratifolium* as an active ingredient.

In one embodiment of the present invention, the extract of *Sargassum serratifolium* may be an extract obtained by using water or an organic solvent.

In one embodiment of the present invention, the organic solvent may be selected from the group consisting of methanol, ethanol, propanol, isopropanol, butanol, acetone, ether, benzene, chloroform, ethyl acetate, methylene chloride, hexane, and cyclohexane.

In one embodiment of the present invention, the extract of *Sargassum serratifolium* may reduce or inhibit the activity of IL-1β, IL-6, or TNF-α, which is an inflammatory cytokine.

In one embodiment of the present invention, the arthritis may be degenerative arthritis, rheumatoid arthritis, or lupus arthritis.

The present invention also provides a health functional food for preventing or ameliorating arthritis, in which the health functional food includes the extract of *Sargassum serratifolium* as an active ingredient Advantageous Effects The present invention relates to a composition for preventing or treating arthritis, in which the composition includes the extract of *Sargassum serratifolium* as an active ingredient. The extract of *Sargassum serratifolium* according to the present invention has excellent activity to reduce or inhibit the activity of IL-1β, IL-6, or TNF-α, an inflammatory cytokine, and has an excellent effect alleviating arthritis in an arthritis animal model so that it can be usefully used as a composition for treating arthritis.

In addition, there is no cytotoxicity, and toxicity to the drug and side effects are avoided, so that it can be safely used even for long-term use, and it is stable in the body.

BEST MODE OF THE INVENTION

The present invention relates to a novel use of the extract of *Sargassum serratifolium* which has proved to be excellent of the extract of *Sargassum serratifolium* for the therapeutic activity of arthritis.

In the present invention, the extract of *Sargassum serratifolium* has received attention as material of a novel therapeutic agent for arthritis, in which *Sargassum serratifolium* is a plant that grows and develops at a range of the intertidal zone to the upper sublittoral belt, which is perennial large brown algae having the length of 1 to 4 m, has a conical root having the diameter of 4 to 5 cm, is like rubber, and has annual rings. The stem thereof has a columnar structure, is divided into many short central branches, and is differentially pressured. Further, both edges thereof are thin, the stem is vertically raised to one side such as midrib, short branches are at the edges, a stem leaf faces at the base, double saw teeth are at the edges, an air bubble is close to a round shape, and there are follicles or thorn-like protrusions at the top thereof. In particular, it is known to grow and develop on the southern coast of Korea and Jeju Island. It is merely known to have functions of lipid lowering, blood pressure lowering, and radioactive isotope release. However, there is no known effect on arthritis.

The present inventors confirmed that the extract of *Sargassum serratifolium* has an activity of treating arthritis according to one embodiment of the present invention. According to one embodiment of the present invention, as a result of the inflammatory cytokine expression level associated with arthritis according to treatment of the extract of *Sargassum serratifolium*, it can be known that the inflammatory cytokine was rapidly increased in the experimental animal group in which rheumatoid arthritis was induced, but the expression of inflammatory cytokines in TNF-α, IL-6 or IL-1β was significantly inhibited in the extract of *Sargassum serratifolium*-treated group of the present invention. In addition, it has been confirmed by experiments that the treatment with the extract of *Sargassum serratifolium* can alleviate arthritis of rheumatoid arthritis experimental animals.

Therefore, the present inventors have found that the extract of *Sargassum serratifolium* has a therapeutic activity against arthritis, and the extract of *Sargassum serratifolium* is more effective than extracts of other *Sargassum*. Therefore, the present inventors have found that the *Sargassum serratifolium* of the present invention is a more useful material for treating arthritis compared to other *Sargassum* species.

Accordingly, the composition comprising the extract of *Sargassum serratifolium* of the present invention as an active ingredient can effectively prevent or treat arthritis.

In the present invention, "arthritis" refers to degenerative arthritis, rheumatoid arthritis, or lupus arthritis, and most preferably, but not limited to, refers to rheumatoid arthritis and degenerative arthritis.

*Sargassum serratifolium* according to the present invention may be used as those obtained by extracting and isolating from nature using an extraction and separation method known in the art, and the "extract" defined in the present invention may be obtained from *Sargassum serratifolium* using a suitable solvent and include, for example, a hot-water extract, a polar solvent-soluble extract, or a non-polar solvent-soluble extract of *Sargassum serratifolium*.

As a suitable solvent for extracting an extract from *Sargassum serratifolium*, any solvent acceptable in the art may be used, and water or an organic solvent may be used. For example, various solvents such as purified water, alcohols having 1 to 4 carbon atoms, such as methanol, ethanol, propanol, isopropanol, and butanol, acetone, ether, benzene, chloroform, ethyl acetate, methylene chloride, hexane, cyclohexane, etc. maybe, but not limited to, used alone or in combination.

As the extraction method, any of methods such as hot water extraction method, cold-immersion extraction method, reflux cooling extraction method, solvent extraction method, steam distillation method, ultrasonic extraction method, dissolution method, and compression method can be selected and used. Further, the desired extract may be further subjected to a conventional fractionation process, and may be purified using a conventional purification method. There is no limitation on the production method of the extract of *Sargassum serratifolium* of the present invention, and any known method can be used.

For example, the extract of *Sargassum serratifolium* in the composition of the present invention is such that the first extract extracted with the hot water extraction method or the solvent extraction method can be prepared in a powder state by an additional process such as vacuum distillation, freeze drying, or spray drying is. Further, the additional purified fraction can be obtained, in which the first extract is treated using various chromatographies such as silica gel column chromatography, thin layer chromatography, and high-performance liquid chromatography.

Therefore, in the present invention, the extract of *Sargassum serratifolium* is a concept including all the extracts, fractions and purifications obtained in each step of extraction, fractionation, or purification, their diluted solutions, concentrates, or dried products.

The composition of the present invention including such extract of *Sargassum serratifolium* as an active ingredient may be a pharmaceutical composition.

The pharmaceutical composition of the present invention may be prepared using pharmaceutically acceptable and physiologically acceptable adjuvants in addition to the above-mentioned active ingredients. Excipients, disintegrants, sweeteners, binders, coating agents, swelling agents, lubricants, glidants, or flavoring agents may be used as adjuvants.

The pharmaceutical composition may be formulated into a pharmaceutical composition containing at least one pharmaceutically acceptable carrier in addition to the above-described active ingredients for administration.

The pharmaceutical composition may be in the form of granules, powders, tablets, coated tablets, capsules, suppositories, solutions, syrups, juices, suspensions, emulsions, drops, or injectable solutions. For example, for formulation into tablets or capsules, the active ingredient may be combined with an oral, non-toxic pharmaceutically acceptable inert carrier such as ethanol, glycerol, and water. Also, if desired or necessary, suitable binders, lubricants, disintegrants, and coloring agents may also be included as a mixture. Suitable binders include, but are not limited to, natural sugars such as starches, gelatin, glucose, and beta-lactose, natural and synthetic gums such as corn sweeteners, acacia, tragacanth and sodium oleate, sodium stearate, magnesium stearate, sodium benzoate, sodium acetate, sodium chloride, and the like. Disintegrants include, but are not limited to, starch, methylcellulose, agar, bentonite, xanthan gum and the like. Acceptable pharmaceutical carriers for compositions that are formulated into a liquid solution include saline, sterile water, ringer's solution, buffered saline, albumin injection solution, dextrose solution, maltodextrin solution, glycerol, ethanol, and a mixture including one or more of these ingredients, which are suitable for the pasteurization and living body. If necessary, other conventional additives such as antioxidants, buffers, and bacteriostatic agents may be added. Further, diluents, dispersants, surfactants, binders and lubricants can be additionally added to formulate into injectable solutions such as aqueous solutions, suspensions, emulsions, pills, capsules, granules, or tablets. Further, it can be preferably formulated according to each disease or ingredient, using methods disclosed in Remington's Pharmaceutical Science, Mack Publishing Company, Easton Pa., as an appropriate method in the relevant field.

In one embodiment of the present invention, the extract of *Sargassum serratifolium* of the present invention may be included in an amount of 0.001% to 20% by weight based on the total weight of the composition. The composition of the present invention may also be a food composition. The food composition may contain, as an additional ingredient, various flavoring agents or natural carbohydrates such as a conventional food composition, in addition containing the extract of *Sargassum serratifolium* as an active ingredient. Examples of the above-mentioned natural carbohydrates include monosaccharides such as glucose and fructose; disaccharides such as maltose and sucrose; and polysaccharides such as conventional sugars, e.g., dextrin and cyclodextrin, and sugar alcohols, e.g., xylitol, sorbitol, and erythritol. The above-mentioned flavoring agents can be advantageously used as natural flavoring agents (taumartin), stevia extracts (e.g., rebaudioside A and glycyrrhizin) and synthetic flavoring agents (e.g., saccharin and aspartame).

The food composition of the present invention can be formulated in the same manner as the pharmaceutical composition and thus used as a functional food or added to various foods. Foods to which the composition of the present invention can be added include, for example, beverages, meat, chocolates, foodstuffs, confectionery, pizza, ramen, other noodles, gums, candy, ice cream, alcoholic beverages, vitamin complexes, and dietary supplement.

Further, the food composition may contain various additives such as various nutrients, vitamins, minerals (electrolytes), flavoring agents such as synthetic flavors and natural flavors, colorants and enhancers (cheese, chocolate, etc.), pectic acid and its salts, alginic acid and its salts, organic acids, protective colloid thickening agents, pH adjusting agents, stabilizers, preservatives, glycerin, alcohols, carbonating agents used in carbonated drinks and the like in addition to the extract of *Sargassum serratifolium* as an active ingredient. Further, the food composition of the present invention may contain fruit for producing natural fruit juice, and fruit juice drinks and vegetable drinks.

Since the extract of *Sargassum serratifolium*, which is an active ingredient of the present invention, is a natural substance and has little toxicity and side effects, it can be safely used for even long-term administration for the purpose of prevention and treatment of arthritis.

The health functional food of the present invention can be manufactured and processed in the form of tablets, capsules, powders, granules, liquids, rings, etc. for the purpose of prevention and treatment of arthritis.

In the present invention, the term "health functional food" refers to foods prepared and processed using raw materials or ingredients having useful functions in accordance with Korean Health Functional Foods Act, No. 6727, which means that it is ingested for the purpose of obtaining a beneficial effect for health use such as control of nutrients or physiological action for the structure and function of the human body.

The health functional food of the present invention may comprise conventional food additives and, unless otherwise specified, whether or not they are suitable as food additives are determined by standard and criteria on corresponding product according to the General Rules and General Test for Korean Food Additives Codex approved by the Korean Ministry of Food and Drug Safety.

Examples of the items listed in the above-mentioned "Food Additives Codex" include chemical compounds such as ketone, glycine, calcium citrate, nicotinic acid, and cinnamic acid; natural additives such as persimmon color, licorice extract, crystalline cellulose, kaoliang color, and guar gum; mixture preparations such as L-glutamic acid sodium preparations, alkali agents for noodles, preservative preparations, and tar coloring preparations.

For example, the extract of *Sargassum serratifolium*, an active ingredient of the present invention, is mixed with the excipient, binder, disintegrant, and other additives, then the mixture is granulated in a usual manner, and then a lubricant and the like is added and the granulate is compression-molded, or then the mixture can be directly compression-molded, thereby obtaining the health functional food in the form of tablet. In addition, the health functional food in the tablet form may contain a flavoring agent or the like as needed.

The hard capsule of the capsule-type health functional food can be prepared by filling a conventional hard capsule with a mixture of the extract of *Sargassum serratifolium*, an active ingredient of the present invention, with an additive such as an excipient. The soft capsule may be prepared by filling a capsule base such as gelatin with a mixture of the extract of *Sargassum serratifolium*, an active ingredient of the present invention, with an additive such as an excipient. The soft capsule may contain plasticizers such as glycerin and sorbitol, coloring agents, preservatives and the like, if necessary.

The ring-type health functional food can be prepared by molding a mixture of the extract of *Sargassum serratifolium*, an active ingredient of the present invention with excipients, binders, disintegrants, and the like, according to a known method. If necessary, it may be coated with white sugars or other coating aids, or the surface thereof may be coated with a material such as starch and talc.

The granule-type health functional food can be prepared by a conventionally known method in which a mixture of the extract of *Sargassum serratifolium*, an active ingredient of the present invention with excipients, binders, and disintegrants is formed into granules. If necessary, fragrance agents, flavoring agents, etc. can be added.

The health functional food may be a beverage, a meat, a chocolate, a foodstuff, a confectionery, a pizza, a ramen, a noodle, a gum, a candy, an ice cream, an alcoholic beverage, a vitamin complex, a health supplement food, etc.

Hereinafter, the present invention will be described in detail with reference to exemplary embodiments. However, these exemplary embodiments are for specifically illustrating the present invention and the scope of the present invention is not limited to these exemplary embodiments.

MODE OF THE INVENTION

Exemplary Embodiment 1

Production of Ethanolic Extract of *Sargassum serratifolium*

*Sargassum serratifolium* used in the present invention were harvested and used in Gijang-gun, Busan City, and the ethanolic extract of *Sargassum serratifolium* was obtained by the following method. First, 2 kg of powder obtained by natural drying *Sargassum serratifolium* in shade or sunny spot and triturating the dried product and 8 liters of alcohol (95% ethanol) were added for the preparation of the ethanolic extract, and the mixture was extracted by a reflux condenser-mounted extractor three times at 70° C. for 3 hours. The foreign substances were removed by filtering the extract with an ultrafilter (MWCO, 50 kDa). The solvent was removed from the filtered extract with a vacuum rotary evaporator at 40° C., and then the extract of *Sargassum serratifolium* was obtained as an extracted residue (200±25 g).

Experimental Example 2

Therapeutic Effect of Ethanolic Extract of *Sargassum serratifolium* on Rheumatoid Arthritis <2-1> Measurement of Weight Change According to Treatment of Extract of *Sargassum serratifolium*

In order to confirm whether or not rheumatoid arthritis can be treated by the extract of *Sargassum serratifolium*, the present inventors first prepared experimental animals in which rheumatoid arthritis was induced.

Eight weeks old Male DBA/1J mice were used and were stabilized and raised for one week. One week later, for DBA/1J mice, an emulsion (CII/CFA) was prepared by mixing and emulsifying complete Freund's adjuvant (CFA) and type II collagen (Bovine type II collagen, 2 mg/mL). 100 µl of CII/CFA was subcutaneously injected into the vein at the lower part of the tail, 2 cm to 3 cm from the tail end of DBA/1J mouse. After 3 weeks of CII/CFA injection, 100 µl of emulsion CII/IFA mixed and emulsified with the same amount of incomplete Freund's adjuvant (IFA) and type II collagen was subcutaneously secondary-injected into the muscle of the DBA/1J mouse, which is the connecting part between the buttocks and the tail. Animal experiments were carried out with the addition of 0.01% (0.024 g/kg of body weight) and 0.05% (0.12 g/kg of body weight) of extracts of *Sargassum serratifolium* prepared by the method of the present invention for 19 days from the day of the second subcutaneous injection.

Figure 1:
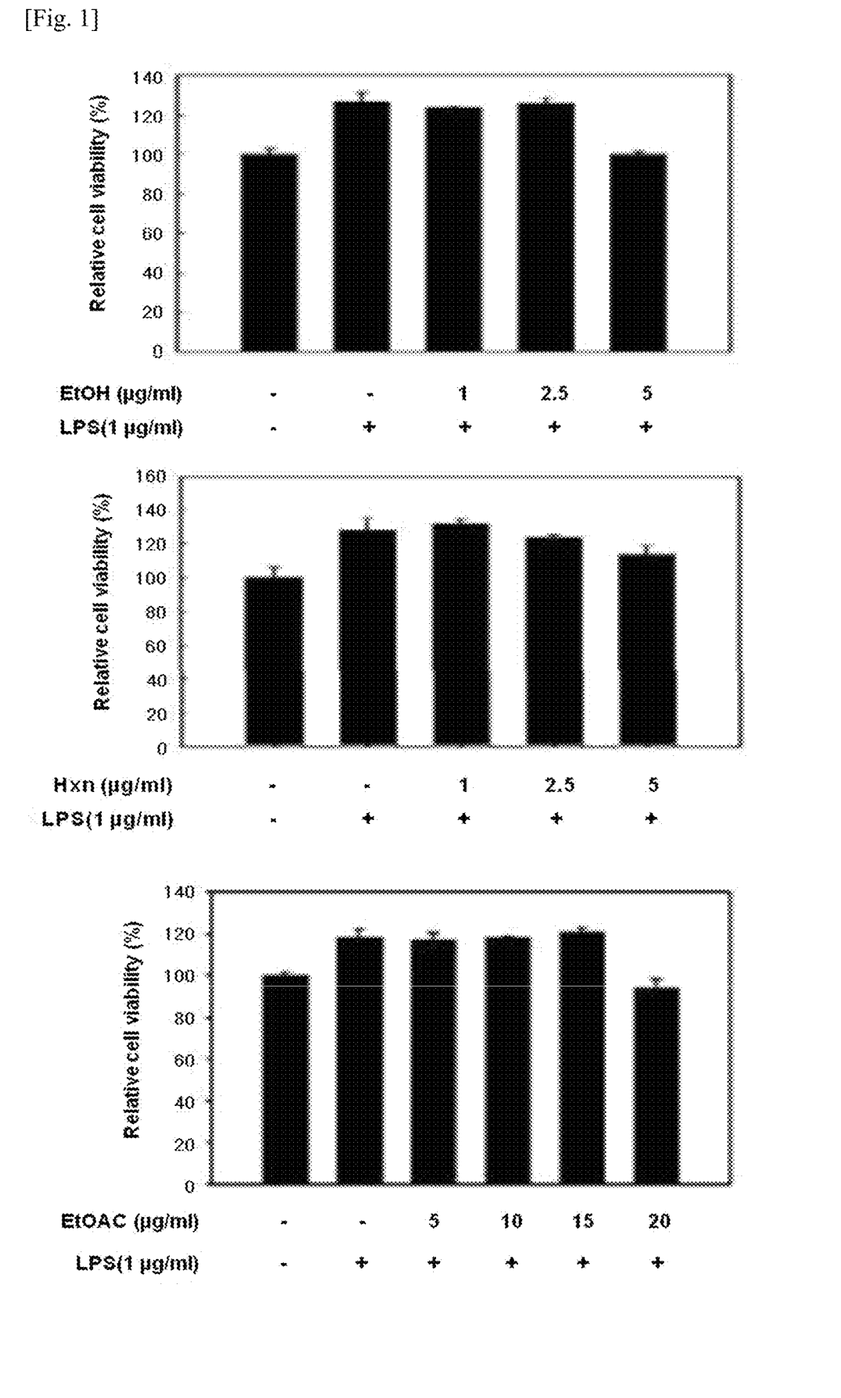
FIG. 1 shows the result of measuring cytotoxicity on cells after treatment with ethanolic (EtOH) extracts of *Sargassum serratifolium* in various concentrations.
Figure 2:
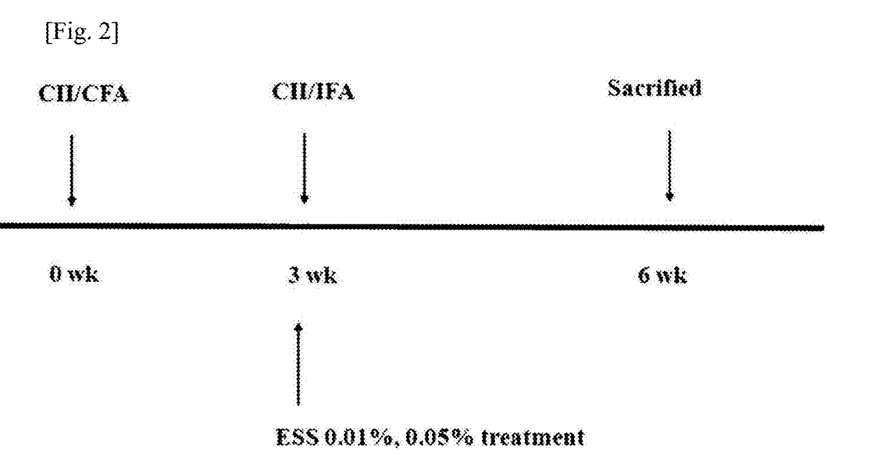
FIG. 2 is a schematic diagram showing a process of preparing an animal model of rheumatoid arthritis.
Figure 3:
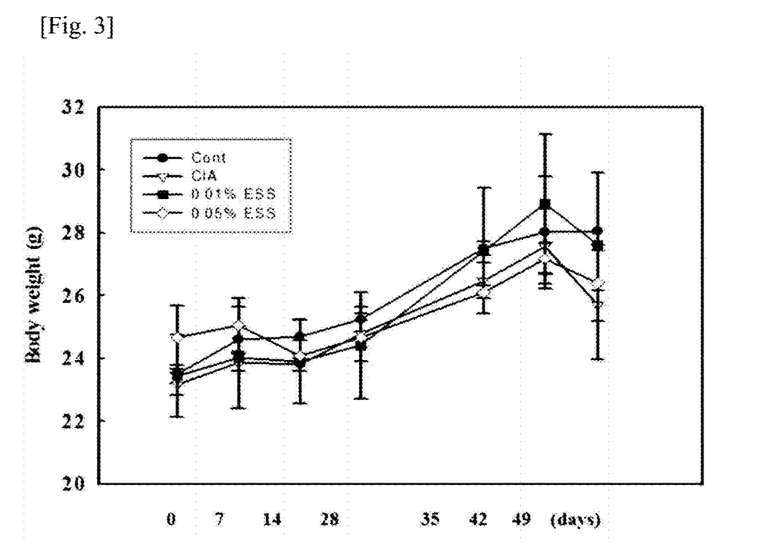
FIG. 3 shows the result of confirming the change in body weight for 6 weeks after administering the extract of *Sargassum serratifolium* of the present invention to rheumatoid arthritis experimental animals.

For the control group without treatment, arthritis animal group (CIA treatment group), and extract of *Sargassum serratifolium*-treated group in which arthritis experimental animals were treated with 0.01% and 0.05% extracts of *Sargassum serratifolium*, their body weights were measured weekly for 7 weeks. As a result, their body weight was slightly increased during the period from 3 weeks to 4 weeks in all groups, but there was no significant change in body weight per group. (See FIG. 3).

<2-2> Measurement of Change of Paw Thickness According to Treatment of Extract of *Sargassum serratifolium*

The present inventors measured the change in paw thickness, which is an index of arthritis, in order to confirm the therapeutic effect of rheumatoid arthritis, caused by the extract of *Sargassum serratifolium*.

The change in paw thickness according to the treatment with the extracts of *Sargassum serratifolium* every 3 days were measured using an electronic caliper for 19 days after the second subcutaneous injection in the preparation process of the experimental animal in which rheumatoid arthritis was induced in <2-1>.

Figure 4:
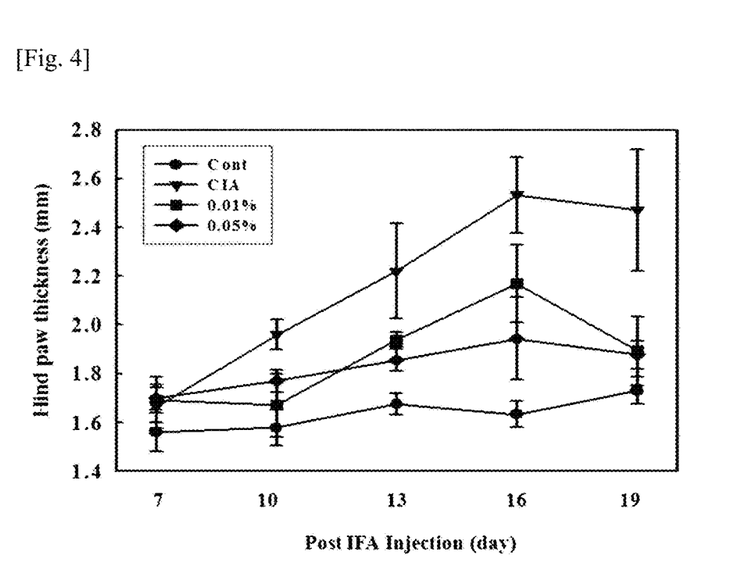
FIG. 4 shows the result of confirming the change in the thickness of the paw after administering the extract of *Sargassum serratifolium* of the present invention to rheumatoid arthritis experimental animals.

As a result, it was found that the paw thickness was increased by inflammation in the experimental animals in which arthritis was induced, whereas the paw thickness was significantly decreased in the group treated with the extract of *Sargassum serratifolium*, and it was confirmed that the thickness thereof after 19 days was similar to that of the control group (See FIG. 4).

<2-3> Measurement of Arthritic Index According to Treatment of Extract of *Sargassum serratifolium*

The present inventors observed the arthritis index by visual inspection in order to confirm the therapeutic effect of the extract of *Sargassum serratifolium* on rheumatoid arthritis, and the arthritis index of each was scored by 0 to 4 points and measured by five non-experts.

The arthritis index was calculated by summing the scores for the respective paws per one number of mouse (highest score=16 points).

—Evaluation Standard—

0 point: there is no symptom;
0.5 point: one finger is red and swelled;
1 point: 2 to 5 fingers are red and a little swelled;
2 points: 2 to 5 joints are red and moderately swelled;
3 points: whole paws are red and swelled; and
4 points: swelling and malformation are reduced.

Figure 5:
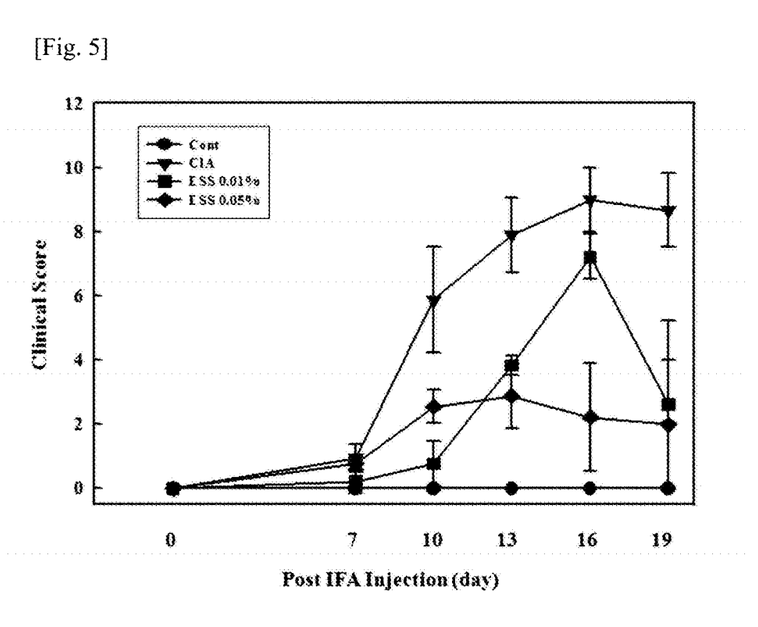
FIG. 5 shows the result of confirming the change in arthritis index after administering the extract of *Sargassum serratifolium* of the present invention to rheumatoid arthritis experimental animals.

As a result of evaluating the rheumatoid arthritis score of each treatment group, it was found that the arthritis index was high in the arthritis-induced experimental animal group, but the arthritis evaluation index was significantly decreased in the treatment group with which the extract of *Sargassum serratifolium* was treated (See FIG. 5).

<2-4> Weighing of Spleen Per Body Weight According to Treatment of Extract of *Sargassum serratifolium*

The present inventors measured the weight of the spleen in order to determine whether or not the extract of *Sargassum serratifolium* can treat rheumatoid arthritis.

A spleen is the major organ of the human immune system, and relative weights are often used as a preliminary indicator to assess the immunoregulatory activity of the sample to be tested.

Figure 6:
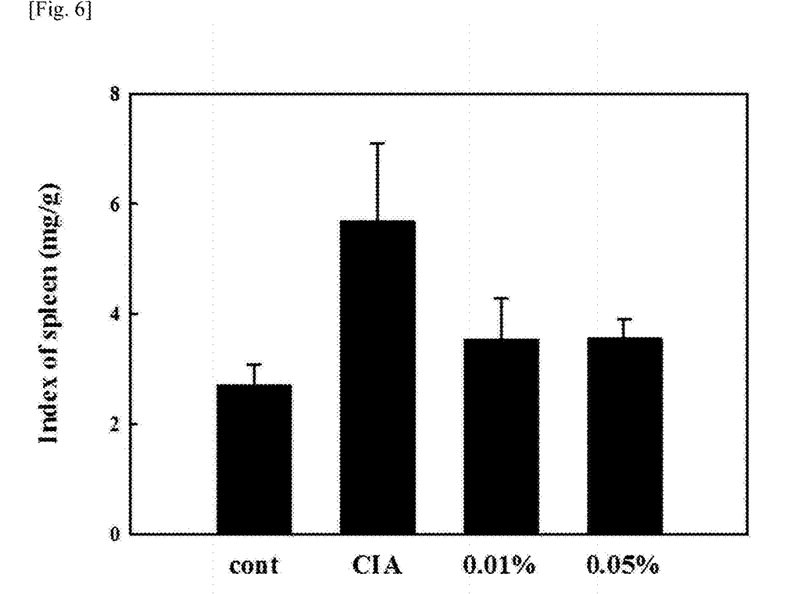
FIG. 6 shows the result of confirming the weight of the spleen per body weight after administering the extract of *Sargassum serratifolium* of the present invention to rheumatoid arthritis experimental animals and then sacrificing the experimental animals at 6 weeks thereafter.

As a result of measuring the weight of the spleen per body weight, the splenoma was found (spleen was swelled and enlarged) in the arthritis-induced experimental animal group, but no splenoma appeared in the group treated with the extract of *Sargassum serratifolium* of the present invention. Thus, it was confirmed that the expansion of the spleen and permeability of immune cells were inhibited by the ethanolic extract of *Sargassum serratifolium* (See FIG. 6).

<2-5> Visual Observation of Level of Arthritis Treatment According to Treatment of Extract of *Sargassum serratifolium*

Figure 7:
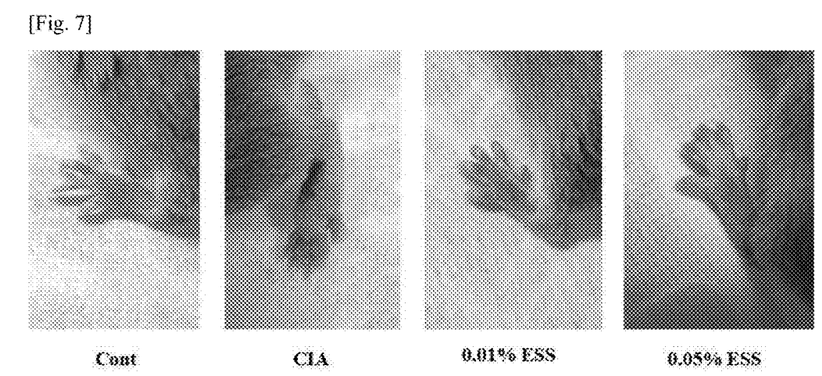
FIG. 7 shows the result of visually confirming the level of arthritis after administering the extract of *Sargassum serratifolium* of the present invention to rheumatoid arthritis experimental animals.

The present inventors observed visually the level of arthritis treatment according to treatment of the extract of *Sargassum serratifolium*. As a result, the hind paw was severely swollen and erythema symptoms were showed in the arthritis-induced experimental animals group. However, it was confirmed that swelling was reduced and erythema symptoms were alleviated in the treatment groups treated with the extract of *Sargassum serratifolium* of the present invention with 0.01% and 0.05% for 19 days (See FIG. 7).

<2-6> Inhibitory Effect of Inflammatory Cytokine According to Treatment of Extract of *Sargassum serratifolium*

When rheumatoid arthritis develops in general, inflammatory mediators such as interleukin (IL) and PGE2 are released into joints and blood by activated immune cells gathered at inflammatory sites. In particular, TNF-α, IL-6, and IL-1β can be used as an index to determine the level of disease of rheumatoid arthritis.

Figure 8:
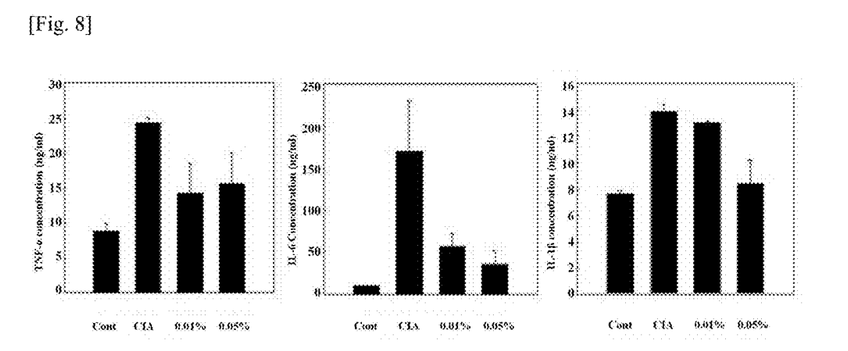
FIG. 8 shows the result of confirming the level of suppression of the production of inflammatory cytokines (IL-1β, IL-6, or TNF-α) in serum after administering the extract of *Sargassum serratifolium* of the present invention to rheumatoid arthritis experimental animals and then sacrificing the experimental animals at 6 weeks thereafter.

The present inventors measured the expression level of the inflammatory cytokine in the blood of an experimental animal using an ELISA kit. As a result, it was confirmed that the inflammatory cytokine rapidly increased in the arthritis-induced experimental animal group, but the expression of inflammatory cytokines in TNF-α, IL-6, or IL-1β was significantly inhibited in the group treated with the extract of *Sargassum serratifolium* of the present invention for 19 days (See FIG. 8).

<2-7> Inhibitory Effect of Inflammatory Cytokine According to Treatment of Extract of *Sargassum serratifolium*

In order to measure the expression level of inflammatory cytokine in the protein extracted by triturating the hind paw which is an inflammatory site, the present inventors measured the expression level by Western blotting.

Figure 9:
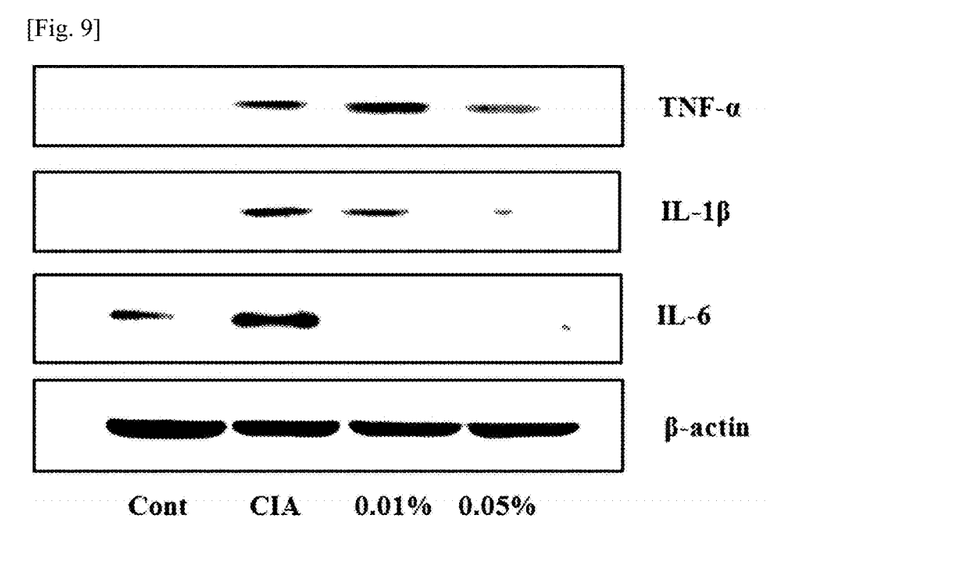
FIG. 9 shows the result of confirming the level of suppression of the production of inflammatory cytokines (IL-1β, IL-6 or TNF-α) in the hind paw, by Western blot, after administering the extract of *Sargassum serratifolium* of the present invention to rheumatoid arthritis experimental animals and then sacrificing the experimental animals at 6 weeks thereafter.

As a result, it was confirmed that the inflammatory cytokine was rapidly increased in the experimental animal group in which rheumatoid arthritis was induced, but the expression of inflammatory cytokines in TNF-α, IL-6, or IL-1β was significantly inhibited in the group treated with the extract of *Sargassum serratifolium* of the present invention (See FIG. 9).

<2-8> Inhibitory Effect of Production of iNOS and COX-2 Proteins According to Treatment of Extract of *Sargassum serratifolium*

NO and PGEs are synthesized from L-arginine and phospholipids by nitric oxide synthase (NOS) and cyclooxygenase (COX), respectively. Under pathological conditions, the excessive increase of NO and PGE2 stimulates the inflammatory process and shows a synergistic effect with other inflammatory mediators. The excessive NO and PGE2 under these conditions are synthesized by inducible NOS (iNOS) and COX-2. In addition, iNOS and COX-2 are strongly expressed when exposed to inflammatory cytokines and bacterial endotoxins.

Thus, the anti-inflammatory effects of the ethanolic extract of *Sargassum serratifolium* on the protein expression of iNOS and COX-2 were observed by Western blot in the hind paw tissue, an inflammatory site of the experimental animals induced by CIA. That is, tissue lysates were obtained for each animal group used in the experiment, and then Western blot was performed using antibodies against iNOS and COX-2.

Figure 10:
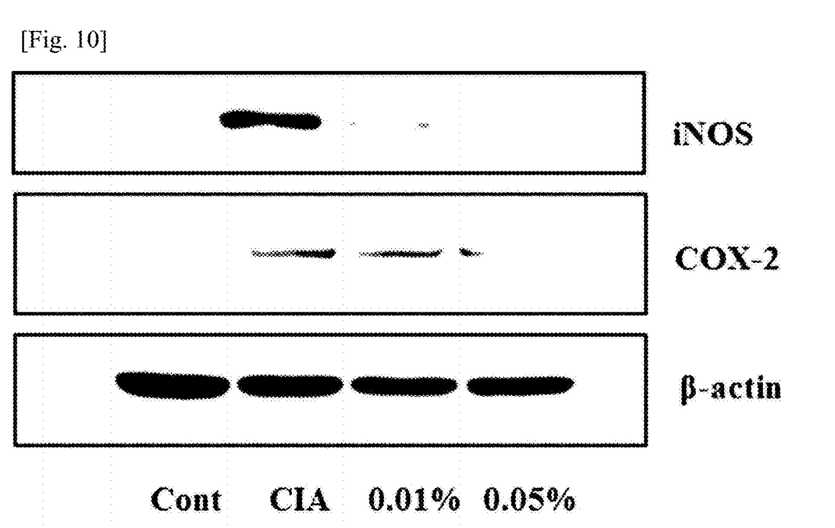
FIG. 10 shows the result of confirming the level of inhibition of the expression of pro-inflammatory proteins (iNOS, COX-2) in the hind paw after administering the extract of *Sargassum serratifolium* of the present invention to rheumatoid arthritis experimental animals and then sacrificing the experimental animals at 6 weeks thereafter.

As a result, as shown in FIG. 10, the ethanolic extract of *Sargassum serratifolium* reduced the expression of iNOS and COX-2 proteins in the joint tissues of the experimental animals induced by CIA treatment in a concentration-dependent manner. These results demonstrate that the ethanolic extract of *Sargassum serratifolium* inhibits the expression of iNOS and COX-2 and thus shows anti-inflammatory effects in joint tissues.

<2-9> Inhibitory Effect of NF-κB Phosphorylation According to Treatment of Extract of *Sargassum serratifolium*

CIA-treated iNOS and COX-2 and the pro-inflammatory cytokines TNF-α, IL-1β, IL-6, etc. are regulated by the transcription factor NF-κB. NF-κB binds with inhibitory κB-α (IκB-α) under normal conditions and thus is inactivated in the cytoplasm. However, when an antigen such as collagen is injected into an animal body, immune cells such as macrophages and monocytes are activated to cause inflammation. This external stimulation activates the inactivated NF-κB in the cell by phosphorylation and thus translocates into the nucleus so that it contributes to the transcription of the inflammation-related protein.

Therefore, in order to confirm whether the ethanolic extract of Sargassum serratifolium of the present invention has an influence on the movement of NF-κB into the nucleus, the present inventors supplied the ethanolic extract of Sargassum serratifolium mixed with feeds to inflammation-induced experimental animals by CIA treatment for 19 days. Western blotting was performed using an antibody against NF-κB phosphorylation after obtaining a tissue lysate from each animal group used in the experimental.

Figure 11:
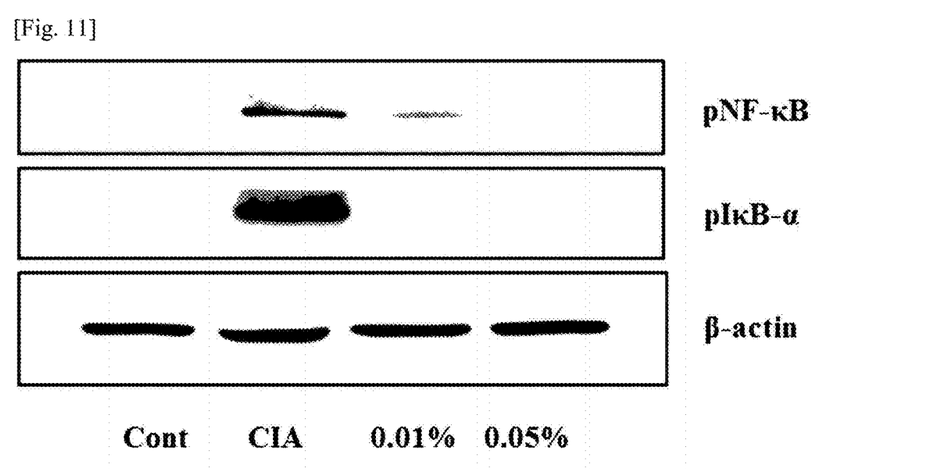
FIG. 11 shows the results of confirming the level of inhibition of the expression of proinflammatory proteins (iNOS, COX-2) in the hind paw after administering the extract of *Sargassum serratifolium* of the present invention to rheumatoid arthritis experimental animals and then sacrificing the experimental animals at 6 weeks thereafter.

As a result, as shown in FIG. 11, NF-κB phosphorylation induced by CIA treatment was decreased in a concentration-dependent manner by the addition of the ethanolic extract of Sargassum serratifolium, and the phosphorylation level shown by the addition of 0.05% of the ethanolic extract was similar to that of the control group.

Thus, through the experimental animals, it was confirmed that the ethanolic extract of Sargassum serratifolium inhibited the phosphorylation of NF-κB in the articular tissues of CIA-induced experimental animals on the experimental to block the activation of NF-κB, which acts as an inflammatory factor such as inflammatory cytokines by movement of NF-κB to the nucleus.

<2-10> Inhibitory Effect of MAPKs and Akt Activation According to Treatment of Extract of Sargassum serratifolium The molecular signaling mechanism that regulates the process of inducing the expression of iNOS or COX-2 or pro-inflammatory cytokines through the activation of NF-κB transcription factors by a variety of external stimuli includes three enzymes belonging to the main MAPK subfamily, namely extracellular-regulated protein kinase (ERK), c-Jun NH2-protein kinase (JNK), p38 MAPK and PI3K/Akt. Western blot was performed to confirm the effect of the ethanolic extract of Sargassum serratifolium of the present invention on the phosphorylation of proteins in the joints.

Figure 12:
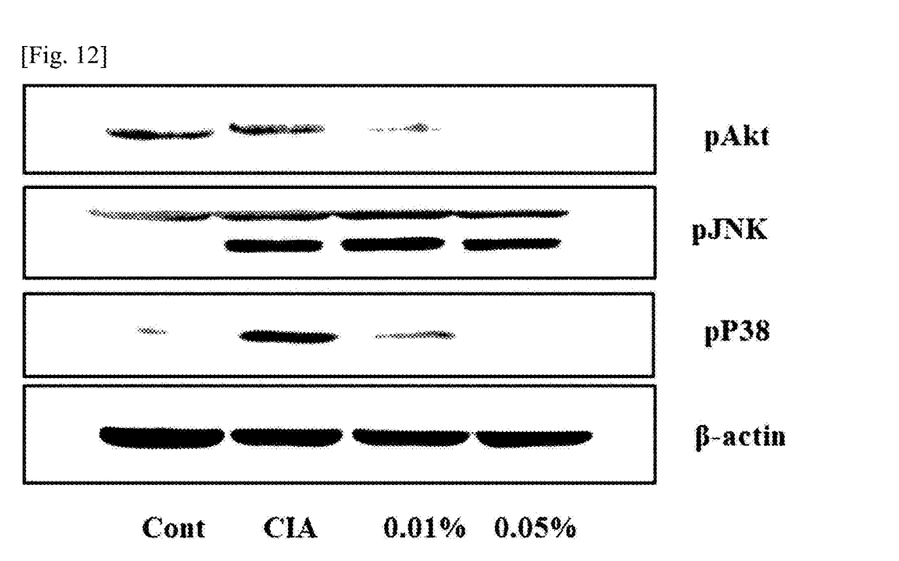
FIG. 12 shows the results of confirming the level of phosphorylation of NF-κB responsible for transcriptional regulation of pro-inflammatory proteins and cytokines in the hind paw after administering the extract of *Sargassum serratifolium* of the present invention to rheumatoid arthritis experimental animals and then sacrificing the experimental animals at 6 weeks thereafter.

As a result, as shown in FIG. 12, it was shown that the ethanolic extract of Sargassum serratifolium inhibited phosphorylation (activation) of Akt, JNK and p38 MAPK in the inflammation response of the experimental animals induced by CIA treatment. Therefore, through the result, it was found that the ethanolic extract of Sargassum serratifolium inhibited the inflammatory response by blocking various signal protein pathways in the joint tissue.

<2-11> Inhibitory Effect of Production of ICAM-1, VCAM-1, MCP-1, MMP-1, 2, and 9 According to Treatment of Extract of Sargassum serratifolium The induction of rheumatoid arthritis by CIA resulted in an increase in the expression of MMP-1, MMP-2 and MMP-9, which degrades cartilage tissue at the joint region, an increase in MCP-1 inducing inflammatory cell infiltration into joint synovial tissue, and an increase in ICAM-1 and VCAM-1, which increase inflammatory cell infiltration into synovial tissues at the joint. Western blotting was performed to confirm the effect of the ethanolic extract of Sargassum serratifolium of the present invention on the inhibition of the production of ICAM-1, VCAM-1, MCP-1, MMP-1, 2, and 9.

Figure 13:
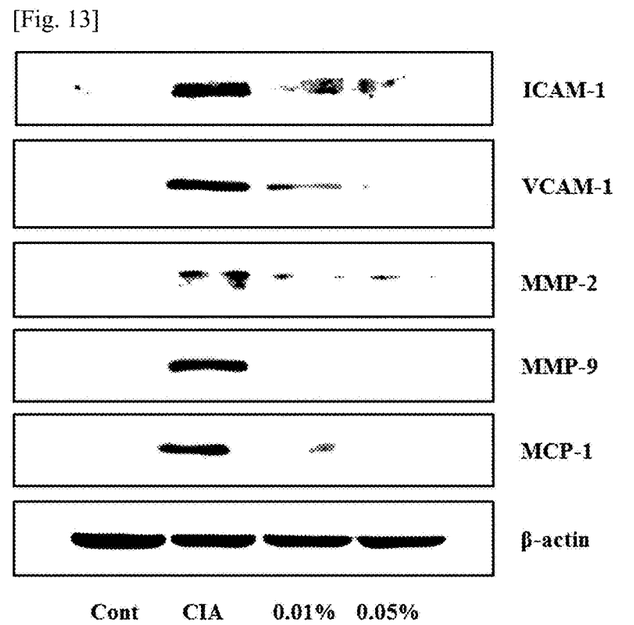
FIG. 13 shows the results of confirming the level of phosphorylation of higher proteins (Akt, JNK, and p38 protein), which are involved in the activation of NF-κB, which is a transcription factor that regulates inflammation in the hind paw after administering the extract of *Sargassum serratifolium* of the present invention to rheumatoid arthritis experimental animals and then sacrificing the experimental animals at 6 weeks thereafter.

As a result, the ethanolic extract of Sargassum serratifolium inhibited the production of ICAM-1, VCAM-1, MCP-1, MMP-1, 2, and 9 in the inflammation response of the experimental animals induced by CIA treatment as shown in FIG. 13. Thus, it was found, through the result, that the ethanolic extract of Sargassum serratifolium inhibited the inflammatory response by blocking various signal protein pathways in the joint tissue.

Experimental Example 3

Confirmation of Arthritis Treatment Effect in Various Sargassum Extracts

The expression level of TNF-α of various inflammatory cytokines was measured using an ELISA kit in order to confirm whether or not arthritis treatment was effective in other Sargassum species as compared with the extract of Sargassum serratifolium of the present invention.

As a result, TNF-α, an inflammatory cytokine, was abruptly increased in the rheumatoid arthritis-induced experimental animal group, but TNF-α expression was decreased when various Sargassum extracts were treated. The arthritis experimental animal group was treated with Sargassum fulvellem, Sargassum horneri, Sargassum yezoense, Sargassum confusum, Sargassum coreanum, Sargassum macrocarpum, Sargassum yendoi, or Myagropsis myagroides, and then the amount of TNF-α expression was examined. As a result, it was found that the amount of TNF-α expression in several Sargassum extracts was inhibited compared to the group which was not treated with Sargassum extracts, and Sargassum serratifolium of the present invention can significantly inhibit the inflammatory cytokine as compared with other Sargassum extracts (See Table 1).

TABLE 1

Inhibitory effect of production of TNF-α of various Sargassum extracts

| Name of Sargassum (Scientific name) | $EC_{50}$ |
|---|---|
| Sargassum serratifolium | 4.6 µg/mL |
| S. fulvellum | 32.4 µg/mL |
| S. horneri | >200 µg/mL |
| S. yezoense | >200 µg/mL |
| S. confusum | 87.6 µg/mL |
| S. coreanum = S. ringgoldianum | >200 µg/mL |
| S. macrocarpum | >200 µg/mL |
| S. yendoi | 62 µg/mL |
| Myagropsis myagroides | 13.5 µg/mL |

Accordingly, it was found that the Sargassum extract of the present invention has an effect of treating arthritis, and in particular, the extract of Sargassum serratifolium of the present invention has higher efficacy than other Sargassum extracts.

Hereinbefore, the present invention has been described with reference to the preferred embodiments. It will be understood by those skilled in the art that the present invention may be embodied in various other forms without departing from the essential characteristics thereof. Therefore, the disclosed embodiments should be considered in an illustrative rather than a restrictive perspective. The scope of the present invention is defined by the appended claims rather than by the preceding description, and all differences within the scope of equivalents thereof should be construed as being included in the present invention.

The invention claimed is:

1. A method for treating rheumatoid arthritis, comprising administering to a patient in need thereof an effective amount of an extract of Sargassum serratifolium as an active ingredient, wherein the extract of Sargassum serratifolium is an extract obtained using an organic solvent selected from the group consisting of methanol, ethanol, acetone, chloroform, ethyl acetate, and hexane.

2. The method of claim 1, wherein the extract of *Sargassum serratifolium* is characterized by reducing or inhibiting the activity of the inflammatory cytokines, IL-1β, IL-6, and TNF-α.

* * * * *